(12) United States Patent
Magno (10) Patent No.: US 10,987,195 B2
(45) Date of Patent: Apr. 27, 2021

(54) ELECTRO-PNEUMATIC DECLOG APPARATUS FOR SURGICAL INSTRUMENT

(71) Applicant: Gyrus ACMI, Inc., Southborough, MA (US)

(72) Inventor: Joey Magno, Cordova, TN (US)

(73) Assignee: Gyrus Acmi, Inc., Southborough, MA (US)

( * ) Notice: Subject to any disclaimer, the term of this patent is extended or adjusted under 35 U.S.C. 154(b) by 63 days.

(21) Appl. No.: 16/257,214

(22) Filed: Jan. 25, 2019

(65) Prior Publication Data

US 2020/0237973 A1  Jul. 30, 2020

(51) Int. Cl.
*A61B 90/70* (2016.01)
*A61B 17/32* (2006.01)
*A61M 1/00* (2006.01)
*F17C 13/04* (2006.01)

(52) U.S. Cl.
CPC ........ *A61B 90/70* (2016.02); *A61B 17/32002* (2013.01); *A61M 1/0023* (2013.01); *A61M 1/0031* (2013.01); *F17C 13/04* (2013.01); *A61B 2217/005* (2013.01); *A61M 2205/7554* (2013.01)

(58) Field of Classification Search
CPC ........ A61B 17/32002; A61B 2217/005; A61B 17/32; A61B 1/125; A61B 2017/32008; A61B 2217/007; A61B 90/70; F17C 13/04; A61M 1/0031; A61M 2205/7554; A61M 1/0084; A61M 39/227; A61M 1/0078; A61M 1/0064; A61M 1/0035; A61M 2205/822; A61M 1/0062
See application file for complete search history.

(56) References Cited

U.S. PATENT DOCUMENTS

2011/0112515 A1   5/2011  Stiehl et al.
2013/0289595 A1  10/2013  Edwards et al.
2014/0207045 A1*  7/2014  Anand ............. A61M 25/0127
                                         604/9

(Continued)

FOREIGN PATENT DOCUMENTS

CN     111494031 A    8/2020
EP       3685867 A1   7/2020
JP     2020116386 A   8/2020

OTHER PUBLICATIONS

"European Application Serial No. 20151326.4, Extended European Search Report dated Jun. 4, 2020", 8 pgs.

(Continued)

*Primary Examiner* — Katherine M Shi
(74) *Attorney, Agent, or Firm* — Schwegman Lundberg & Woessner, P.A.

(57) ABSTRACT

A medical device includes a first valve and a second valve. The first valve includes a manifold having a first opening, a second opening, and a third opening, and an element movable within the manifold and spring-biased to close the first opening. When biased to close the first opening, air flows from the second opening to the third opening. The second valve is configured to provide a flow of pressurized gas to the first valve to move the element to close the third opening. The first valve and the second valve are configured, upon moving the element to close the third opening, to interrupt the flow of air from the second opening to the third opening and to allow the flow of the pressurized gas to exit the second opening.

20 Claims, 6 Drawing Sheets

(56) References Cited

U.S. PATENT DOCUMENTS

2015/0073364 A1* 3/2015 Cheng ................ A61M 1/0031
                                                    604/319
2018/0147022 A1* 5/2018 Gupta .................... A61B 1/122

OTHER PUBLICATIONS

"European Application Serial No. 20151326.4, Response filed Jan. 27, 2021 to Extended European Search Report dated Jun. 4, 2020", 12 pgs.

* cited by examiner

ELECTRO-PNEUMATIC DECLOG APPARATUS FOR SURGICAL INSTRUMENT

BACKGROUND

Field of the Invention

The exemplary and non-limiting embodiments described herein relate generally to devices and methods that relate to the clearing of obstructions from surgical instruments during surgical procedures. The exemplary and non-limiting embodiments described herein relate more particularly to a compressed gas-operated valve that facilitates the clearing of suction lines during use of a tissue debriding instrument.

Brief Description of Prior Developments

Debridement involves the controlled, surgical removal of damaged tissue from a wound to promote wound healing. Types of debridement techniques in current use include sharp, autolytic, chemical, mechanical, and biologic debridement. Sharp debridement techniques employ sharp devices hereinafter referred to as "debriders" that are used by surgeons to cut necrotic, infected, or otherwise damaged tissue away from healthy tissue. These debriders may be simple bladed instruments such as curettes or scalpels. More complex debriders may include ports in the blades and associated lines to supply fluid for wound irrigation and/or for suction to carry debrided tissue away from the wound during debridement procedures.

Debriders equipped with suction typically clog with debrided tissue when large amounts of the tissue are drawn up. Older debriders often required the use of a stylet to clear a clog. More up-to-date debriders generally include an in-line valve that operates by squeezing a pressure bulb to purge the clog back through the blade. These in-line mechanisms are generally known as "decloggers."

SUMMARY

In accordance with one aspect, a medical device comprises a first valve and a second valve. The first valve comprises a manifold having a first opening, a second opening, and a third opening, and an element movable within the manifold and spring-biased to close the first opening. When biased to close the first opening, air flows from the second opening to the third opening. The second valve is configured to provide a flow of pressurized gas to the first valve to move the element to close the third opening. The first valve and the second valve are configured, upon moving the element to close the third opening, to interrupt the flow of air from the second opening to the third opening and to allow the flow of the pressurized gas to exit the second opening.

In accordance with another aspect, a medical system comprises a first valve configured to allow a first flow of air in a first direction and selectively allow a second flow of gas in a second direction; a console comprising a second valve operably connected to the first valve and configured to provide the second flow of gas in the second direction; and a surgical instrument operably connected to the first valve and having a cutting assembly from which the first flow of air is received, the surgical instrument configured to receive the second flow of gas in the second direction. The first valve and the second valve are configured to allow the second flow of gas in the second direction to clear an obstruction from the cutting assembly of the surgical instrument during an operation of the surgical instrument.

In accordance with another aspect, a medical system comprises a first valve having a first connection port, a second connection port, and a third connection port, wherein the second connection port and the third connection port are configured to allow a flow of air by suction in a first direction; a console having a second valve operably connected to the first connection port, a pressure regulator connected to the second valve, and a gas source connected to the pressure regulator, wherein the console is configured to allow a flow of gas from the gas source through the first connection port and to the second connection port in a second direction that is opposite to the first direction; and a surgical instrument operably connected to the second connection port and having a cutting assembly from which the first flow of air by suction is received, the surgical instrument configured to receive the flow of gas from the gas source through the second connection port. The first valve and the second valve are configured to allow the flow of gas through the second connection port to clear an obstruction from the cutting assembly of the surgical instrument during an operation of the surgical instrument.

In accordance with another aspect, a method of clearing an obstruction from a surgical instrument comprises providing the surgical instrument having a cutting assembly; providing a manifold valve configured to be switchable between a first configuration and a second configuration; providing a solenoid valve coupled to the manifold valve; providing a source of pressurized gas coupled to the solenoid valve and configured to flow through the solenoid valve to the manifold valve; and actuating the manifold valve and the solenoid valve to cause the flow through the manifold valve to clear an obstruction from the cutting assembly of the surgical instrument.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
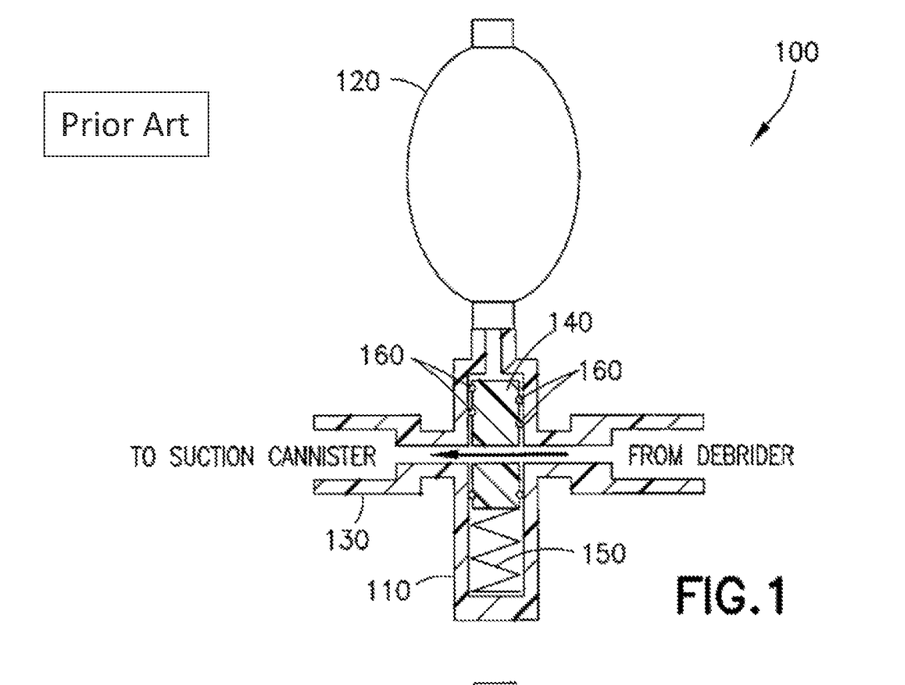
FIG. 1 is a cross-sectional view of a declog valve actuatable by a manually-operated pressure bulb.
Figure 2:
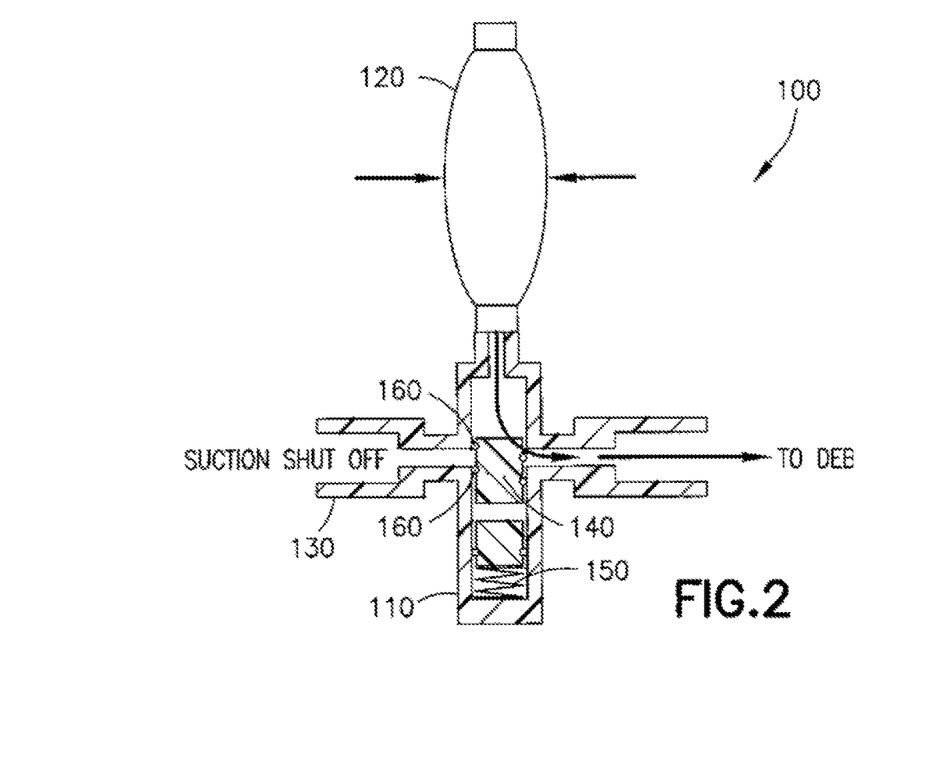
FIG. 2 is a cross-sectional view of the declog valve of FIG. 1 with the manually-operated pressure bulb compressed.

Referring to FIGS. 1 and 2, production versions of current decloggers 100 for debriders equipped with suction generally consist of a 3-way 2-position valve 110 operated by a pressure bulb 120. As shown in FIG. 1, when the pressure bulb 120 is not being operated, suction is applied to the debrider through a suction line 130. As shown in FIG. 2, operating the pressure bulb 120 by manually squeezing by a user, such as a surgeon, actuates a declogging function by shifting a spool 140 from a "home" position to close the suction line 130 and directing air pressure from the pressure bulb 120 to the debrider to purge out the clog through a window in the blade of the debrider. Once the air pressure is released, the spool 140 is returned to the home position by a compression spring 150. Such a configuration functions to remove tissue clogging the debrider or in the suction line extending from the debrider. The debrider is thereby purged or "declogged" during use.

Current spool-type designs generally employ angled O-rings 160 located circumferentially around the spool 140. Movement of the spool 140 may cause uneven compression of the O-rings 160 with regard to sealing, which may result in higher tolerance requirements and the use of excessive lubricant (such as grease) to assist in the sealing.

Figure 3:
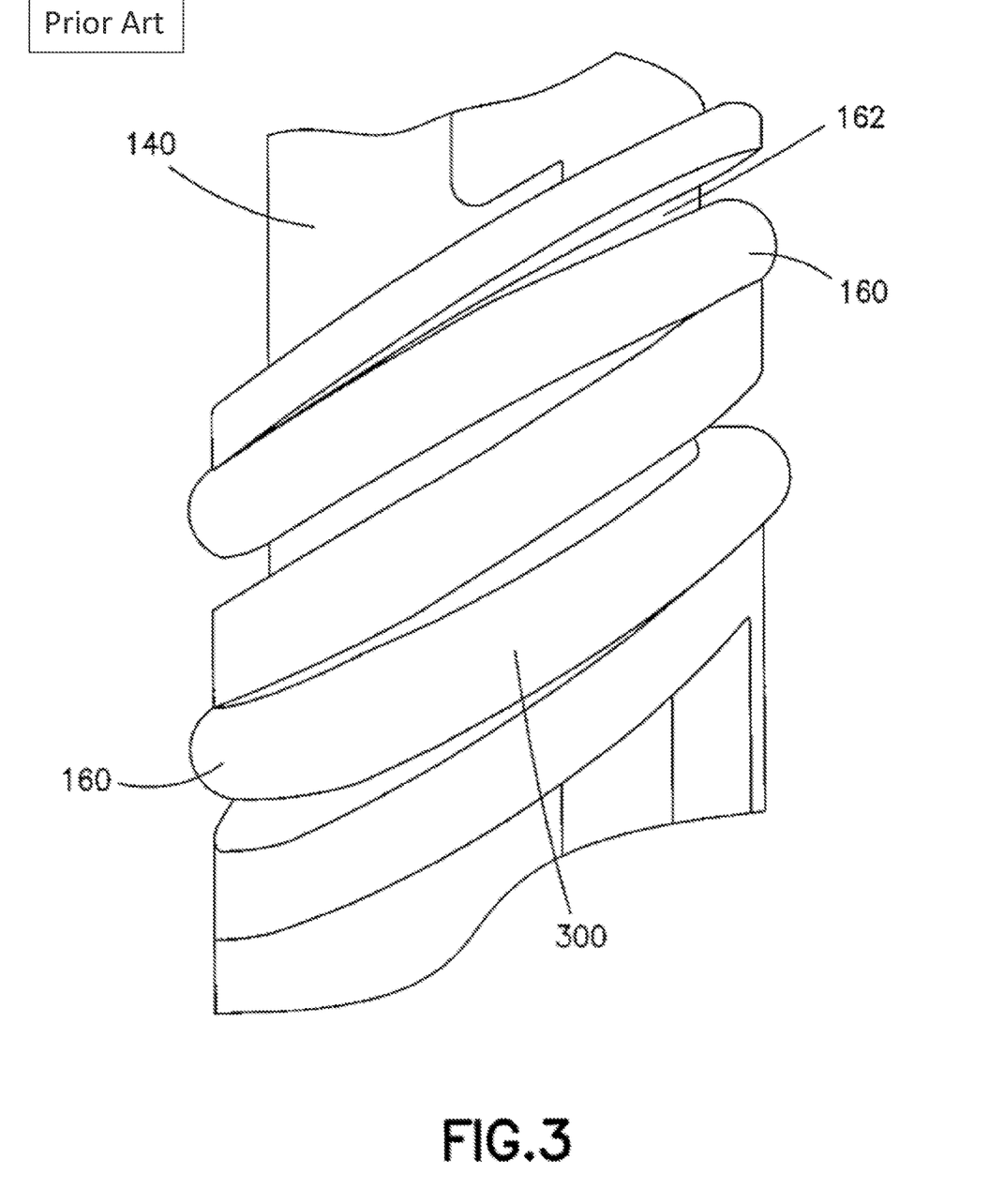
FIG. 3 is a side view of a spool of the declog valve of FIG. 1 illustrating uneven compression and stretching of O-rings.

Referring to FIG. 3, uneven compression of the O-rings 160 is shown at 300. In a dynamic application of the declogger 100 utilizing the spool 140, the O-rings 160 are preferably not stretched over 5% on their diameters. As shown, the diagonal design stretches each O-ring over 11% on its diameter due to the effective circumference of the spool 140 being larger than the O-ring 160. This causes a reduction in cross-sectional area of the O-ring 160 and further deforms it into an elliptical shape, which results in an irregular cross section when the O-ring 160 is viewed along the housing bore. Furthermore, in a dynamic application, the O-rings 160 should be compressed at least 10-15%. As shown, each O-ring 160 is compressed at most 3%. Moreover, in the embodiments described herein, the O-rings 160 work best under higher pressures, for example, from about 100 pounds per square inch (psi) to about 3000 psi, to compress against glands 162 formed by grooves in the spool 140 in which the O-rings 160 are positioned and the inside diameter of walls of the bore in which the spool 140 translates to seal effectively. Current applications that utilize the pressure bulb 120 may operate at about 25 psi and may experience negative pressures due to suction, which renders the ability to provide sealing much less effective. When the O-rings 160 are unevenly compressed, an increased squeeze force may be required on the pressure bulb 120 to actuate the spool 140, and if the valve is not operated for a long period of time without any actuation, the declogger 100 may require a much higher squeeze pressure just to initially cause the O-rings 160 to dynamically "break away" from the seals. This phenomenon is known as "stiction," which is the friction which tends to prevent stationary surfaces from being set in motion.

Figure 4:
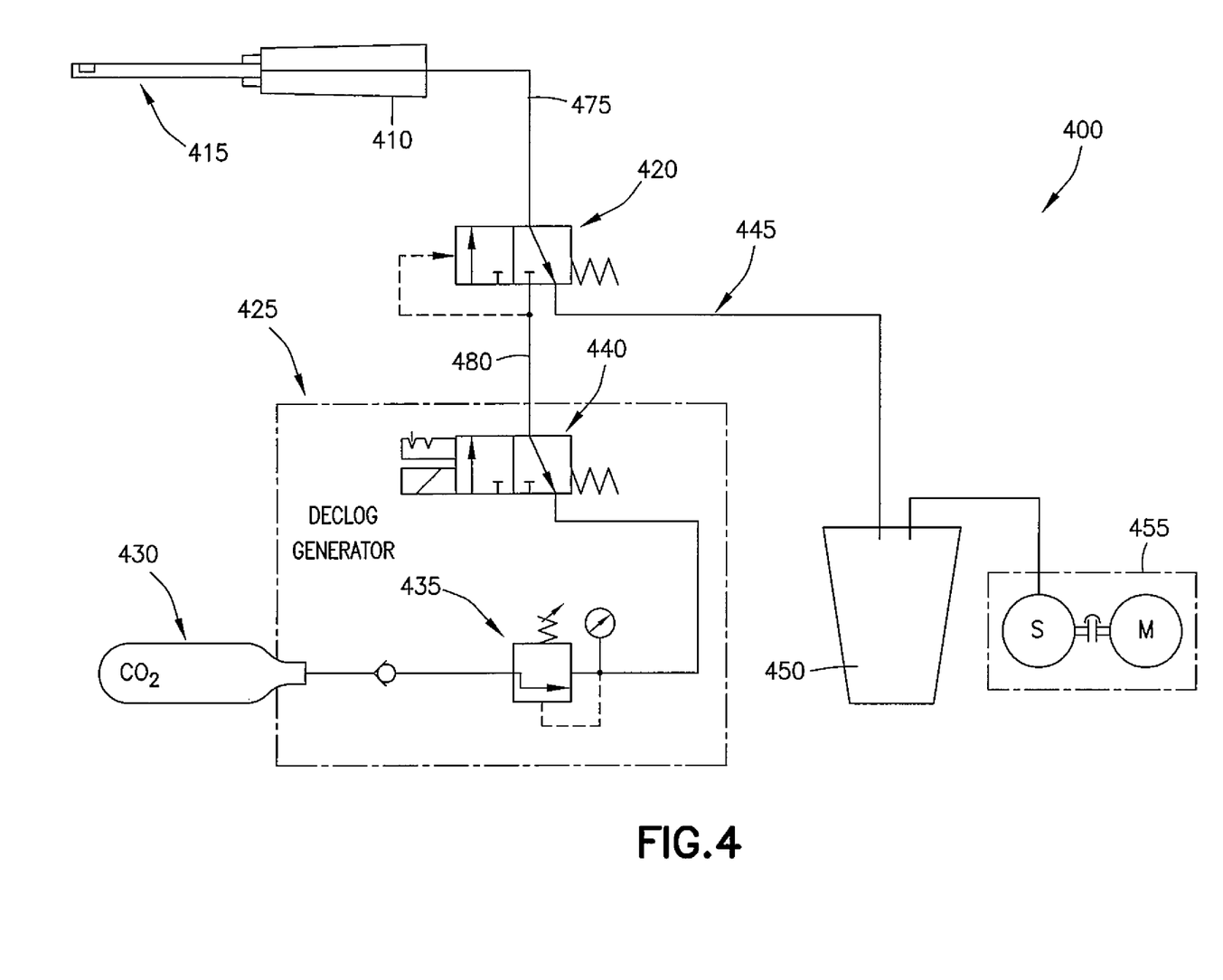
FIG. 4 is a schematic representation of a system incorporating a debrider, a pilot-operated declog valve, and a console.

One proposed solution may eliminate the manual operation of squeezing the pressure bulb 120 by eliminating the pressure bulb 120 itself. Referring to FIG. 4, one exemplary embodiment of a system 400 is shown, the system 400 incorporating a debrider 410 having a blade 415 with a window, a 3-way/2-position declog valve 420, and a control console 425. The system 400 may be used in conjunction with methods of clearing obstructions (such as debrided tissue) from the debrider 410 (or other surgical instrument). The declog valve 420 may be pilot-operated, for example, remotely pneumatically actuated.

In system 400, the control console 425 includes a cartridge 430 having pressurized gas, a pressure regulator 435, and a solenoid-operated 3-way/2-position valve 440 (hereinafter "solenoid valve 440"). The cartridge 430 provides medical grade $CO_2$ (or another gas such as nitrogen, nitrous oxide, or air) that is regulated by the pressure regulator 435 operated at a pre-determined pressure setting to provide a more consistent application of gas for declogging procedures. The cartridge 430, which may be disposable, is installed in the console 425 by any suitable means (such as a threaded screw) and is replaced whenever cartridge pressure falls below a minimum level. The pressure regulator 435 and the solenoid valve 440 are fixedly located inside the console 425 as part of a unit device. The connections of a declog line 480 to the declog valve 420 and the console 425 may be made using push in connectors or the like. The debrider 410 may be connected to the declog valve 420 through a device line 475, also using push in connectors.

Using the $CO_2$ from the cartridge, a user-operated declog function is carried out by the declog valve 420, the declog valve 420 being coupled to a suction line 445 that terminates in a suction canister 450 and pump 455 similar to systems that employ existing decloggers. In the system 400, however, the weight thereof will be less since the pressure bulb is eliminated.

In methods of clearing obstructions (declogging) using the system 400, the solenoid valve 440 receives electrical signals either by hardwire or wirelessly by a push button switch located in a hand piece or at a footswitch associated with the debrider 410 and operated as desired by the user. Pulses of compressed $CO_2$ gas from the cartridge 430 are then metered by the solenoid valve 440 and delivered to the declog valve 420. Any or all of the debrider 410, the declog valve 420, and the solenoid valve 440 may be associated with a controller having a processor and memory, the memory including software. The operations of the solenoid valve 440 and the declog valve 420 may be controlled using the controller. The solenoid valve 440 may have a manual override if the user desires to opt out of control thereof using the controller.

Figure 5A:
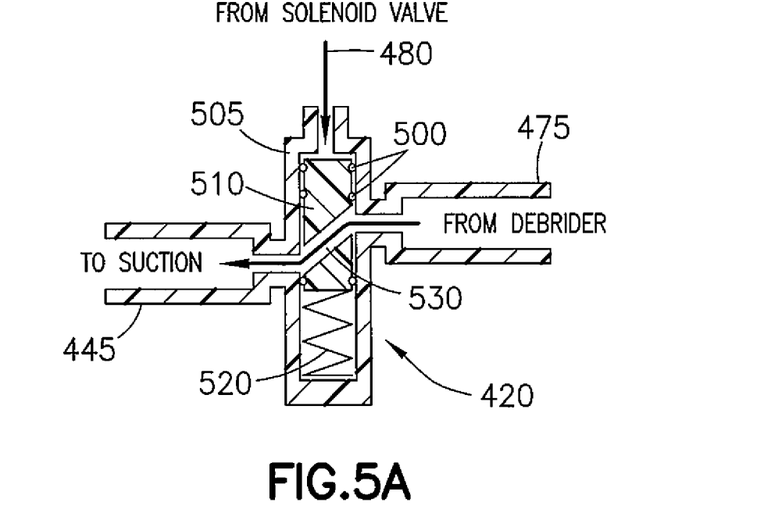
FIGS. 5A and 5B are cross-sectional views of one exemplary embodiment of a declog valve actuatable by compressed gas.
Figure 5B:
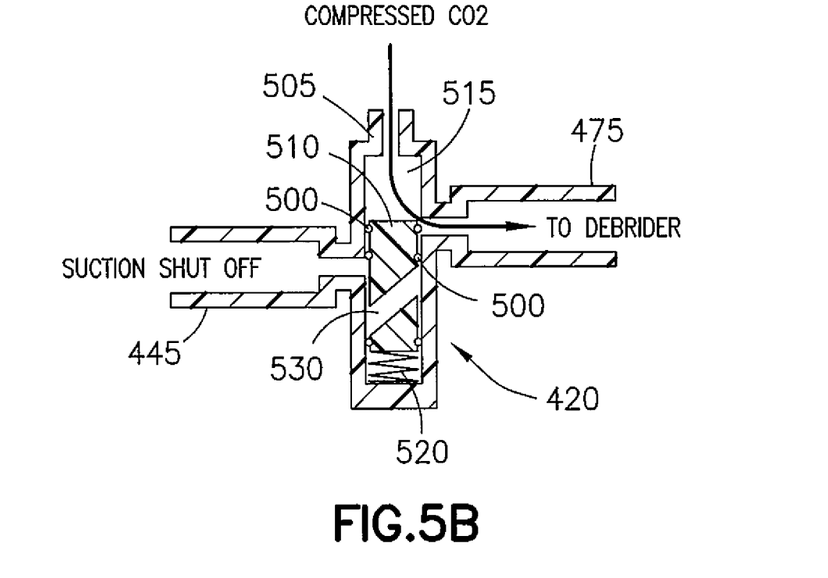

Referring to FIGS. 5A and 5B, in one exemplary embodiment, the declog valve 420 may be improved over previous designs to compensate for the angling of the O-rings. The declog valve 420 comprises a housing 505 having a substantially cylindrical structure. In the declog valve 420, O-rings 500 are positioned on a spool 510 configured to translate in a bore 515 formed lengthwise in the housing 505 and forming a manifold, the spool 510 being biased in the bore 515 from one end via a spring 520 or the like, with the O-rings 500 being substantially transverse to the directions of travel of the spool 510 in an effort to avoid deformation of the O-rings 500. Also, instead of a pressure bulb actuating the solenoid valve, the declog valve 420 is coupled at one end of the housing 505 to the declog line 480 from the solenoid valve 440 to receive the compressed $CO_2$ gas. Proper pressure and timing regarding opening and closing of the solenoid valve 440 may be used to determine optimal efficiency settings to ensure that the declog function will purge the most difficult clogs that the debrider 410 will encounter.

As shown in FIG. 5A, the spool 510 includes a cross-bore 530 extending therethrough, the cross-bore 530 extending across the spool 510 and being angled relative to the sides of the spool 510 such that upon the spring 520 biasing the spool 510 to open the suction (spool 510 is in the "home" position), the suction line 445 coupled to one side of the housing 505 and the device line 475 coupled to an opposing side of the housing 505 from the declog valve 420 are offset.

As shown in FIG. 5B, upon the solenoid valve 440 being actuated to release the compressed $CO_2$ from the cartridge 430, the spool 510 is translated through the bore 515 and the spring 520 compressed. In doing so, the spool 510 closes the suction line 445 and extends a sufficient distance past the opening of the device line 475 extending to the debrider 410 such that $CO_2$ can flow through the device line 475 and to the debrider 410 to purge a clog. The coupling of the declog line 480 from the solenoid valve 440 to the end of the housing 505, the coupling of the suction line 445 to the side of the housing 505, and the coupling of the device line 475 to the opposing side of the housing 505 provide three openings to define the "3-way" aspect of the declog valve 420, and the "home" and extended positions of the spool 510 define the "2-position" aspect of the declog valve 420. Air pressure boosters or amplifiers may also be incorporated into the declog valve 420 to translate the spool 510.

Figure 6:
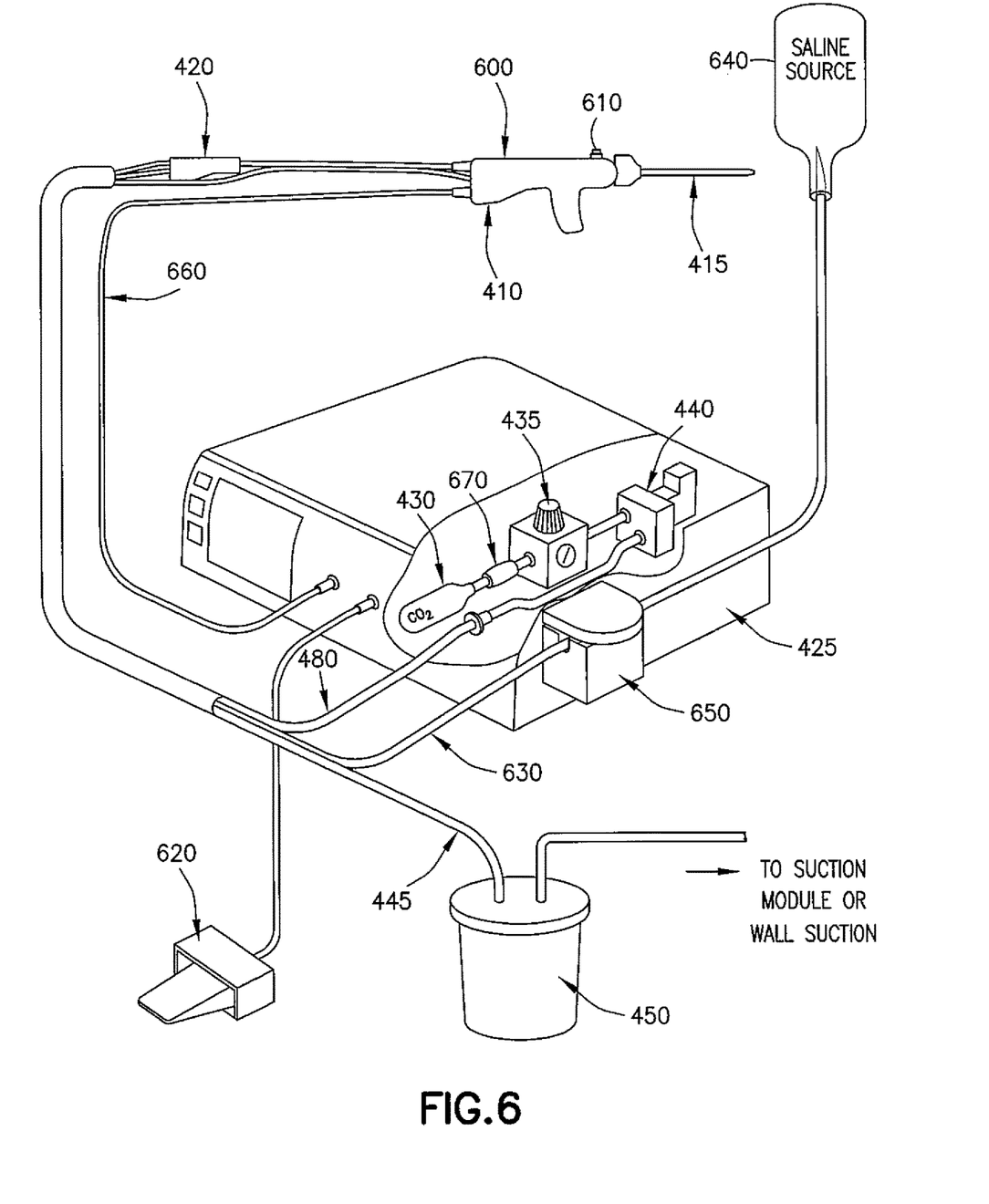
FIG. 6 is a perspective and partial cutaway view of the proposed system of FIG. 4.

Referring to FIG. 6, one exemplary configuration of the system 400 showing relative positions of the debrider 410, the declog valve 420, and the console 425 is depicted. As can be seen, the debrider 410 includes a handle 600 on which a switch 610 configured to operate the declog valve 420 is mounted. The declog valve 420 may also, or alternately, be operated via a foot switch 620 operably coupled to the console 425. A forward end of the declog valve 420 is located at the end of the device line 475, which may be flexible, extending from the debrider 410. A rearward end of the declog valve 420 is coupled to the suction line 445 and also to the solenoid valve 440 in the console 425 via the declog line 480. An irrigation line 630 may extend from an irrigation source 640 along the suction line 445 and the declog line 480, bypassing the declog valve 420 and, extending to the debrider 410. A peristaltic pump 650 may be located in the irrigation line 630 to pump irrigation fluid (such as saline) to the debrider 410. A power line 660 may also extend to the debrider 410. The cartridge 430 may be coupled to the pressure regulator 435 in the console 425 through a check valve 670.

Figure 7A:
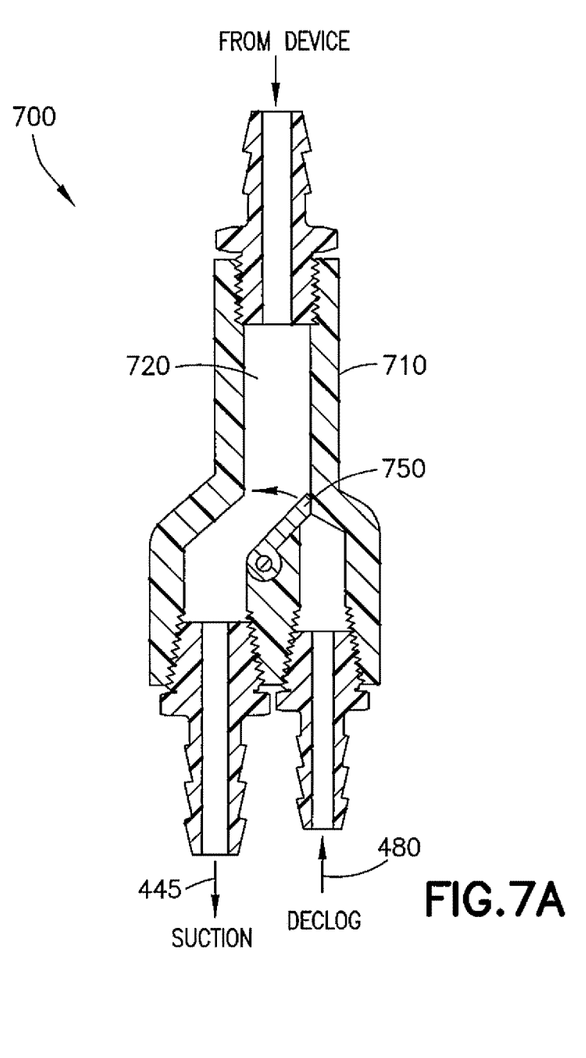
FIG. 7A is a side sectional view of another exemplary embodiment of a declog valve.
Figure 7B:
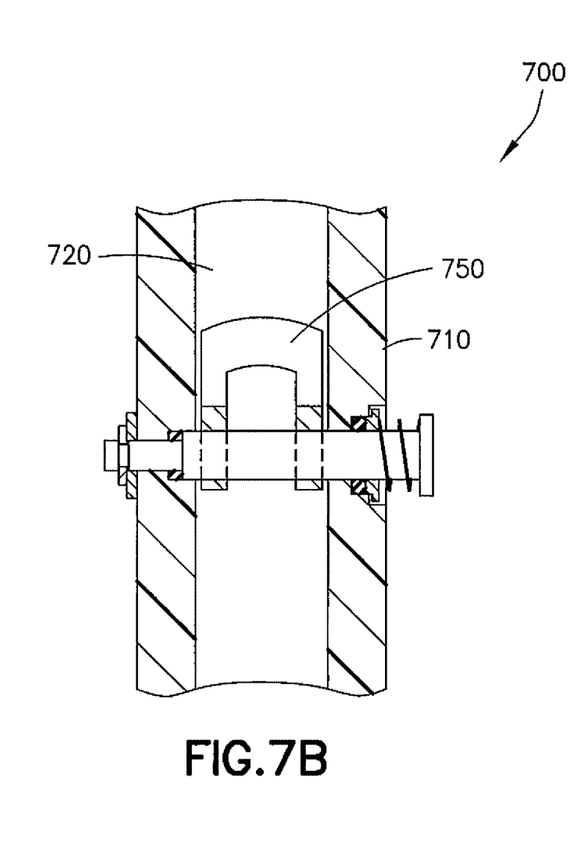
FIG. 7B is a front sectional view of the declog valve of FIG. 7A using a butterfly valve instead of a spool.

Referring now to FIGS. 7A and 7B, another exemplary embodiment of the declog valve is shown generally at 700. The declog valve 700 comprises a body 710 having a manifold defined by a Y-shaped bore 720 extending therethrough with an opening at a forward end being attachable to the device line 475 (which may be coupled to a debrider) and two openings at a rearward end, one opening at the rearward end being attachable to a suction line 445 and the other opening at the rearward end being attachable to a declog line 480. The declog line 480 is coupled to a console having a cartridge (such as a $CO_2$ source) and a solenoid valve. A spring-loaded flapper valve 750 is positioned in the body 710 and between the two openings at the rearward end. The spring-loaded flapper valve 750 is biased to close the opening at the rearward end coupled to the declog line 480, thus allowing suction to be maintained in the device line 475.

The user operates the declog valve 700 to purge a clog by triggering the solenoid valve in the console, which causes the flow of gas from the cartridge, which pressurizes the declog line 480 and opens the spring-loaded flapper valve 750 and urges it against a wall in the bore 720, thereby closing the suction line 445. Upon release of a mechanism triggering the solenoid valve, the flow of gas from the cartridge is stopped, the declog line 480 is depressurized, and the spring-loaded flapper valve 750 is allowed to return to its biased position closing the opening at the rearward end coupled to the declog line 480.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

In one exemplary embodiment, a medical device comprises a first valve and a second valve. The first valve, comprises a manifold having a first opening, a second opening, and a third opening, and an element movable within the manifold and spring-biased to close the first opening. When biased to close the first opening, air flows from the second opening to the third opening. The second valve is configured to provide a flow of pressurized gas to the first valve to move the element to close the third opening. The first valve and the second valve are configured, upon moving the element to close the third opening, to interrupt the flow of air from the second opening to the third opening and to allow the flow of the pressurized gas to exit the second opening.

The flow of air from the second opening to the third opening may be a flow of air from a cutting assembly of a surgical device caused by suction at the third opening. The flow of pressurized gas to the first valve to move the element to close the third opening may be further directed to the cutting assembly of the surgical device to purge an obstruction in the surgical device. The flow of pressurized gas to the first valve may be from a $CO_2$ cartridge. In some embodiments, the element movable within the manifold may be a spool slidable within a bore. The spool may include at least one O-ring transverse to a direction of travel of the spool. The flow of pressurized gas to the first valve may be at least 100 pounds per square inch. In other embodiments, the element movable within the manifold may be a flapper.

In another exemplary embodiment, a medical system comprises a first valve configured to allow a first flow of air in a first direction and selectively allow a second flow of gas in a second direction; a console comprising a second valve operably connected to the first valve and configured to provide the second flow of gas in the second direction; and a surgical instrument operably connected to the first valve and having a cutting assembly from which the first flow of air is received, the surgical instrument configured to receive the second flow of gas in the second direction. The first valve and the second valve, are configured to allow the second flow of gas in the second direction to clear an obstruction from the cutting assembly of the surgical instrument during an operation of the surgical instrument.

The first flow of air in the first direction may be from suction applied to the first valve. In some embodiments, the first valve may comprise a spool that is slidable in a bore, wherein when the spool is in a first position the first flow of air is allowed and wherein when the spool is moved to a second position the second flow of gas is allowed. The spool may be sealed to a wall defining the bore and may be slidable in the bore using at least one O-ring. The second flow of gas in the second direction may be from a source of compressed gas. The source of compressed gas may be a $CO_2$ cartridge. The source of compressed gas may be at at least 100 pounds per square inch. In other embodiments, the first valve may comprise a flapper that is movable in a bore, wherein when the flapper is in a first position the first flow of air is allowed and wherein when the flapper is moved to a second position the second flow of gas is allowed.

In another exemplary embodiment, a medical system comprises a first valve having a first connection port, a second connection port, and a third connection port, wherein the second connection port and the third connection port are configured to allow a flow of air by suction in a first direction; a console having a second valve operably connected to the first connection port, a pressure regulator connected to the second valve, and a gas source connected to the pressure regulator, wherein the console is configured to allow a flow of gas from the gas source through the first connection port and to the second connection port in a second direction that is opposite to the first direction; and a surgical instrument operably connected to the second connection port and having a cutting assembly from which the first flow of air by suction is received, the surgical instrument configured to receive the flow of gas from the gas source through the second connection port. The first valve and the second valve are configured to allow the flow of gas through the second connection port to clear an obstruction from the cutting assembly of the surgical instrument during an operation of the surgical instrument.

In some embodiments, the first valve may comprise a spool that is slidable in a bore, wherein when the spool is in a first position the flow of air by suction in the first direction is allowed and wherein when the spool is moved to a second position the flow of gas from the gas source to the second connection port in a second direction is allowed. The spool may be sealed to a wall defining the bore and may be slidable in the bore using at least one O-ring. The gas source may be a compressed gas at at least 100 pounds per square inch. The gas source may be compressed $CO_2$. In other embodiments, the first valve may comprise a flapper that is movable in a bore, wherein when the flapper is in a first position the flow of air by suction in the first direction is allowed and wherein when the flapper is moved to a second position the flow of gas to the second connection port in a second direction is-allowed.

In another exemplary embodiment, a method of clearing an obstruction from a surgical instrument comprises providing the surgical instrument having a cutting assembly; providing a manifold valve configured to be switchable between a first configuration and a second configuration; providing a solenoid valve coupled to the manifold valve; providing a source of pressurized gas coupled to the solenoid valve and configured to flow through the solenoid valve to the manifold valve; and actuating the manifold valve and the solenoid valve to cause the flow through the manifold valve to clear an obstruction from the cutting assembly of the surgical instrument.

Actuating the manifold valve may comprise applying the pressurized gas to switch the manifold valve from a first configuration in which air flows by suction in a first direction from the cutting assembly to a second configuration in which the pressurized gas flows in a second direction opposite to the first direction to the cutting assembly to clear the obstruction. The source of pressurized gas may be a $CO_2$ cartridge. The pressurized gas may be at at least about 100 pounds per square inch.

It should be understood that the foregoing description is only illustrative of the invention. Various alternatives and modifications can be devised by those skilled in the art without departing from the invention. Accordingly, the invention is intended to embrace all such alternatives, modifications, and variances which fall within the scope of the appended claims.

What is claimed is:

1. A medical device, comprising:
   a first valve, tethered with a handheld portion of the medical device, the first valve comprising,
   a manifold having a first opening, a second opening, and a third opening, and
   a plug movable within the manifold and spring-biased to close the first opening, wherein when biased to close the first opening air flows from the second opening to the third opening;
   a compressed gas reservoir located remote from the first valve and the handheld portion of the medical device;
   a second valve located remote from the first valve configured to provide a flow of pressurized gas from the compressed gas reservoir and through a conduit to the first valve to move the plug to close the third opening;
   wherein the first valve and the second valve are configured, upon moving the plug to close the third opening, to interrupt the flow of air from the second opening to the third opening and to allow the flow of the pressurized gas to exit the second opening.

2. The medical device of claim 1, wherein the flow of air from the second opening to the third opening is a flow of air from a cutting assembly of a surgical device caused by suction at the third opening.

3. The medical device of claim 2, wherein the flow of pressurized gas to the first valve to move the plug to close the third opening is further directed to the cutting assembly of the surgical device to purge an obstruction in the surgical device.

4. The medical device of claim 1, wherein the plug movable within the manifold is a spool slidable within a bore.

5. The medical device of claim 4, wherein the spool includes at least one O-ring defining a plane that is perpendicular to a direction of travel of the spool.

6. The medical device of claim 5, further comprising the flow of pressurized gas to the first valve is having the pressure of at least 100 pounds per square inch.

7. The medical device of claim 6, wherein the compressed gas reservoir is a $CO_2$ cartridge.

8. The medical device of claim 1, wherein the plug movable within the manifold is a flapper.

9. The medical device of claim 1, further comprising an actuator located local to the first valve on the handheld portion of the medical device and configured to remotely actuate the second valve.

10. The medical device of claim 9, wherein the actuator is configured to send an electrical signal by hardwire to the second valve for remote actuation.

11. The medical device of claim 9, wherein the actuator is configured to send an electrical signal wirelessly to the second valve for remote actuation.

12. The medical device of claim 1, further comprising an actuator located remote from the first valve configured to remotely actuate the second valve.

13. The medical device of claim 1, further comprising controller circuitry configured to control operation of the second valve.

14. The medical device of claim 1, wherein the compressed gas reservoir and the second valve are located at a control console, the control console being operably connected to the handheld portion of the medical device.

15. A medical device, comprising:
   a first valve, comprising,
   a manifold having an inner surface, a first opening, a second opening, and a third opening, and
   a plug slidingly connected to the inner surface of the manifold and spring-biased to close the first opening, wherein when biased to close the first opening a suction channel is established between the second opening to the third opening; and a seal member located circumferentially around the plug between the plug and the manifold, the seal member configured to produce a fluidic seal between the first opening and the second opening;

wherein the seal member defines a plane perpendicular to a direction of travel of the plug through the manifold;

a second valve located remote from the first valve and configured to release a flow of pressurized gas through a conduit to the first valve to move the plug to block the suction channel; and wherein the first valve and the second valve are configured, upon moving the plug to block the suction channel, to break the fluidic seal between the first opening and the second opening thereby establishing a purge channel and allowing the flow of the pressurized gas to exit the second opening.

16. The medical device of claim 15, wherein the seal member is stretched circumferentially around the plug at less than 105% of an original diameter.

17. The medical device of claim 15, further comprising a flow of pressurized gas to the first valve having a pressure of at least 100 pounds per square inch, wherein the flow of pressurized gas further compresses the seal member.

18. The medical device of claim 15, wherein the seal member is compressed at least 10% of an original thickness.

19. The medical device of claim 15, further comprising a groove disposed circumferentially around the plug configured to accept the seal member.

20. The medical device of claim 15, wherein the fluidic seal between the first opening and the second opening is restored upon the plug returning to a biased position.

* * * * *

UNITED STATES PATENT AND TRADEMARK OFFICE
CERTIFICATE OF CORRECTION

PATENT NO. : 10,987,195 B2
APPLICATION NO. : 16/257214
DATED : April 27, 2021
INVENTOR(S) : Joey Magno Page 1 of 1

It is certified that error appears in the above-identified patent and that said Letters Patent is hereby corrected as shown below:

In the Claims

In Column 8, Line 33, in Claim 6, after "valve", delete "is"

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*